United States Patent
Zhu et al.

(10) Patent No.: US 6,734,212 B2
(45) Date of Patent: May 11, 2004

(54) METHODS AND COMPOSITIONS FOR TREATING OR PREVENTING BACTERIAL INFECTION

(75) Inventors: Dexu Zhu, Jiangsu Province (CN); Mitsumi Muramatsu, Tokushirma (JP); Jianshu Xie, Shanghai (CN); Cheng Ni, Jiangsu Province (CN); Ming-Wei Wang, San Diego, CA (US)

(73) Assignees: Shanghai East Best Biopharmaceutical, Shanghai (CN); Nanjing University, Nanjing (CN)

( * ) Notice: Subject to any disclaimer, the term of this patent is extended or adjusted under 35 U.S.C. 154(b) by 0 days.

(21) Appl. No.: 09/975,136

(22) Filed: Oct. 10, 2001

(65) Prior Publication Data
US 2003/0125384 A1 Jul. 3, 2003

(51) Int. Cl.$^7$ .................. A61K 31/24; C07C 229/00; C07C 279/00; A61B 17/06
(52) U.S. Cl. .................. 514/535; 514/538; 560/34; 562/439; 206/438
(58) Field of Search .................. 562/439; 560/34; 514/538, 535; 206/438

(56) References Cited

U.S. PATENT DOCUMENTS

| | | | | |
|---|---|---|---|---|
| 4,191,779 A | | 3/1980 | Cook et al. .................. 424/319 |
| 4,732,916 A | * | 3/1988 | Satoh et al. | |
| 4,954,512 A | * | 9/1990 | Oguro et al. | |
| 5,376,655 A | | 12/1994 | Imaki et al. ............. 514/237.5 |
| 5,571,674 A | | 11/1996 | Hoshina et al. ................ 435/6 |
| 5,686,102 A | | 11/1997 | Gross et al. ................ 424/450 |
| 5,736,154 A | | 4/1998 | Fuisz ......................... 424/449 |
| 5,741,511 A | | 4/1998 | Lee et al. .................... 424/449 |
| 5,886,039 A | | 3/1999 | Kock et al. .................. 514/557 |
| 5,941,868 A | | 8/1999 | Kaplan et al. .............. 604/500 |
| 6,197,801 B1 | | 3/2001 | Lin ............................ 514/365 |
| 6,258,374 B1 | | 7/2001 | Friess et al. ................ 424/436 |
| 6,284,791 B1 | * | 9/2001 | Kamoda et al. | |

FOREIGN PATENT DOCUMENTS

| | | | |
|---|---|---|---|
| JP | 63218652 A2 | * | 9/1988 |
| WO | WO 01/44815 | | 6/2001 |

OTHER PUBLICATIONS

Sperl et al, Proceedings of the National Academy of Sciences of the United States of America, (4–aminomethyl)Phenylguanidine Derivatives as Nonpeptide Highly Selective Inhibitors of Human Urokinase 2000, 97(10), pp. 5113–5118.*
Aspinall et al., Glycobiology (1999) 9(11):1235–1245.
Chopra et al., Antimicrob. Agents Chemother. (1997) 41:497–503.
DeLoney and Schiller, Antimicrob. Agents Chemother. (2000) 44 (12):3368–3373.
De Ungria et al., Plasmid. (1999) 41(2):97–109.
Enroth et al., Clin. Infect. Dis. (1999) 28(6):1305–1307.
Enroth et al., Cancer Epidemiol. Biomakers Prev. (2000) 9(9):981–985.
Fassbinder et al., FEMS Microbiol. Lett. (2000) 191(2):191–197.
Gschwantler et al., Eur. J. Gastroenterol. Hepatol. (1998) 10(7):579–582.
Hua et al., Helicobacter. (1999) 4(1):28–32.
Hua et al., Eur. J. Gastroenterol. Hepatol. (2000) 12(10):1129–1134.
International Agency for Research on Cancer. World Health Organization, Lyon, France, Monograph on the evaluation of carcinogenic risk to humans. (1994) 61:177–240.
Irisawa et al., Biol. Pharm. Bull. (1993) 16:621–626.
Irisawa et al., Biol. Pharm. Bull. (1993) 16:1211–1215.
Israel et al., Clin. Invest. (2001) 107(5):611–620.
JAMA (1994) 272:65–69.
Jasny and Hines, Science (1999) 286:443–491.
Jiang et al., J. Biochem. (1998) 124:980–985.
Kato et al., Eur. J. Biochem. (1992) 210:1007–1014.
Kato et al., Biol. Pharm. Bull. (1993) 16:552–557.
Kato et al., J. Enzyme Inhibition (1994) 8:25–37.
Kato et al., Biol. Pharm. Bull. (1998) 16:120–124.
Lyon and Skurray, Microbiol. Rev. (1987) 51:88–134.
Matsui et al., Dig. Dis. Sci. (2000) 45(1):49–54.
Monteiro et al., Eur. J. Biochem. (2000) 267(2):305–320.
Neu, Science (1992) 257:1064–1073.
Nogrady, Medicinal Chemistry: A Biochemical Approach, Oxford University Press, New York, (1985) pp. 388–392.
Occhialini et al., Infect. Immun. (2000) 68(11):6240–6249.
Peek et al., Cancer Res. (1999) 59(24):6124–6131.

(List continued on next page.)

Primary Examiner—Johann Richter
Assistant Examiner—Paul A. Zucker
(74) Attorney, Agent, or Firm—Morrison & Foerster LLP

(57) ABSTRACT

The invention relates to compositions and methods for treating or preventing disease or disorders caused by or associated with certain bacterial infection, especially *Escherichia coli* (*E. coli*) or *Helicobacter pylori* (*H. pylori*) infection. One exemplary compound of the present invention has the following formula I:

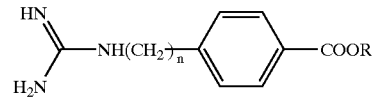

wherein n is 0 or 1, and R is selected from the group consisting of $C_{1-10}$ alkyl, $C_{6-10}$ aryl and

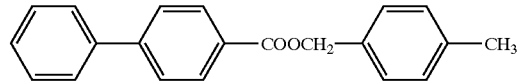

and wherein when n is 0, R is not $C_{6-10}$ aryl.

18 Claims, 3 Drawing Sheets

OTHER PUBLICATIONS

Peek, Jr., J. Physiol. Gastrointest. Liver Physiol. (2001) 280(4):G525–530.
Petersen et al., FEMS Immunol. Med. Microbiol. (2000) 29(1):59–67.
Queiroz et al., J. Infect. Dis. (2000) 181(2):626–630.
Rasko et al., Eur. J. Biochem. (2000) 267:6059–6066.
Van Doorn et al., Clin. Exp. Immunol. (1999) 115(3):421–427.
Van Doorn et al., Infect. Immun. (1999) 67(6):3040–3046.
Vitkute et al., Bacteriol. (2001) 183(2):443–450.
Wang et al., J. Immunol. (2001) 167(2):926–934.
Warren et al., Lancet (1983) 1:1273–1275.
Zwet et al., Lancet (1998) 352:1595.

* cited by examiner

METHODS AND COMPOSITIONS FOR TREATING OR PREVENTING BACTERIAL INFECTION

TECHNICAL FIELD

The invention relates to compositions and methods for treating or preventing diseases or disorders caused by or associated with certain bacterial infection, especially *Escherichia coli* (*E. coli*) or *Helicobacter pylori* (*H. pylori*) infection.

BACKGROUND ART

Ever since antibiotics became commercially available in the 1940s, they were regarded as magic bullets in eliminating bacteria without doing many harms to the patients. However, with each passing decade, an increasing number of antibiotics are no longer effective against a rising number of antibiotic resistant strains. Infections such as tuberculosis and pneumonia are becoming untreatable as they were before the discovery of antibiotics. We are now confronted with a serious worldwide public health crisis (Neu, Science, 257:1064–1073, (1992))

Since the discovery of penicillin in 1929, we now have over 150 antibiotics. They belong to several classes of antibiotics and have different mechanism of actions (Lyon and Skurray, Microbiol. Rev., 51:88–134, (1987)). In general, these compounds are made by living organisms that inhibit growth and proliferation of bacteria. For example, vancomycin and β-lactam can block cell wall synthesis (Chopra et al., Antimicrob. Agents Chemother., 41:497–503, (1997); and Nicolaou et al., Scientific American, 48–52 May (2001)). Erythromycin and tetracycline can disrupt protein synthesis. Sulfonamide interferes with folic acid metabolism, rifampin can block RNA synthesis, and quinolone inhibits DNA replication.

To combat the bacterial resistance, new approaches of treating bacteria infections are under research and development. These new approaches involve giving new life to existing antibiotics such as molecular alteration. Recently, a new class of antibiotics "self-assembling peptide nanotubes" generated interests (Associated Press New, Jul. 25, 2001). This compound uses rings of microscopic amino acids that form tubes to push through the surface of bacterium. There are also many new developments in the genomic areas. They entail interfering with bacterial RNA (rRNA) and messenger RNA (mRNA). A new technique called in vivo expression technology (IVET) that can tag bacteria genes is also under research. In addition, a promising approach is the antisense therapy for treating bacterial infections (Jasny et al., Science, 286:443–491, (1999)).

A class of antibacterial which seems to target a specific protease involved in DNA synthesis has been identified (Kato et al., *Biol. Pharm. Bull.*, 16:120–124 (1998); Irisawa et al., *Biol. Pharm. Bull.*, 16:621–626 (1993); Irisawa et al., *Biol. Pharm. Bull.*, 16:1211–1215 (1993); Kato et al., *J. Enzyme Inhibition*, 8:25–37 (1994); Kato et al., *Eur. J. Biochem.*, 210:1007–1014 (1992); and (Kato et al., *Biol. Pharm. Bull.*, 16:552–557 (1993)). This class of compounds, which acts as competitive trypsin inhibitors in vitro, is made up of various aromatic esters of trans-4-guanidinomethylcyclohexanecarboxylic acid (GMCHA) (See the following formula I):

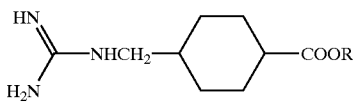

*Helicobacter pylori* (*H. pylori*), a gram-negative spiral bacterium, was first isolated from a patient with chronic gastritis by Warren and Marshall in 1983 (Warren et al., Lancet, 1:1273–1275 (1983)). A lot of evidence has showed close relationship between gastroduodenal disease and *H. pylori*. Thus, it is assumed that *H. pylori* is an important bacterial pathogen which induces chronic gastritis and is associated with gastroduodenal ulcer, adenocarcinoma of the distal stomach, and gastric lymphoma in humans. Recently, the World Health Organization classified *H. pylori* as a group 1 carcinogen responsible for its leading role in the development of gastric cancer (International Agency for Research on Cancer. World Health Organization, Lyon, France, Monograph on the evaluation of carcinogenic risk to humans. 61:177–240,1994).

In 1994, National Institute of Health (NIH) recommended a regimen with simultaneous administration of proton-pump inhibitor (PPI) and antibacterial agent to eradicate *H. pylori* (*Helicobacter Pylori* in peptic ulcer disease: NIH consensus development panel on *Helicobacter Pylori* in peptic ulcer disease. (*JAMA*, 272:65–69 (1994)). Since then, oral administration of metronidazole, PPI, and clarithromycin and amoxicillin is put to practice, being able to cure the infection in up to 80–90% of the cases. However, the application of antibacterial agents causes a serious problem which induces the resistant strain of *H. pylori* to the reagent. Actually, the resistant strains to methonidazole, clarithromycin and amoxicillin have already been reported (Zwet et al., Lancet, 352:1595 (1998)). Other severe problems caused by the administration of PPI and antibacterial agent are that PPI induces indigestion and large amounts of antibacterial agent result severe in destruction of the bacterial flora in digestive tract.

Therefore, it is very important to find out a new type of active anti-bacteria compound. The present invention addresses this and other related needs in the art.

DISCLOSURE OF THE INVENTION

The present invention adds to the repertoire of anti-bacteria agents by providing drugs which would inhibit DNA replication initiation in certain bacteria. In one aspect, the present invention is directed to a compound, or a pharmaceutically acceptable salt thereof, having the following formula II:

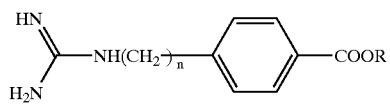

wherein n is an integer from 0–1, and R is elected from the group consisting of hydrogen, $C_{1-10}$ alkyl, $C_{1-10}$ aryl and

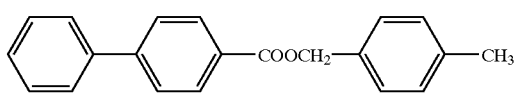

Preferably, the compound has the following formula III (NE-2001):

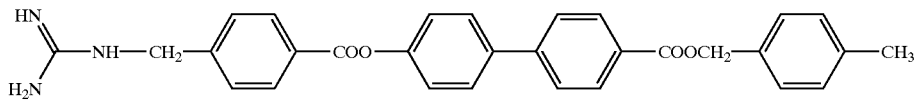

Also preferably, the compound, or its pharmaceutically acceptable salt thereof, is provided in the form of a pharmaceutical composition, either alone or in combination with a pharmaceutically acceptable carrier or excipient. Kits comprising the above compounds for treating or preventing a disease or disorder caused by or associated with bacterial infection, e.g., E. coli or H. pylori infection, are also provided.

In another aspect, the present invention is directed to a method for treating or preventing a disease or disorder caused by or associated with bacterial infection, which method comprises administering, to a subject to which such treatment or prevention is needed or desirable, an effective amount of an agent that selectively inhibits bacterial DNA replication initiation, or a pharmaceutically acceptable salt thereof, thereby said disease or disorder is treated or prevented. Preferably, the disease or disorder is caused by or associated with E. coli or H. pylori infection. Also preferably, the disease or disorder caused by or associated with the bacterial, especially, E. coli or H. pylori infection, is treated or prevented by administering to the subject an effective amount of a compound, or a pharmaceutically acceptable salt thereof, having the following formula II:

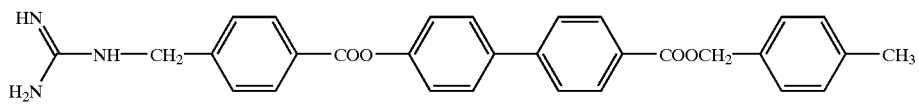

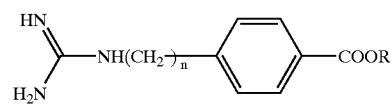

wherein n is an integer from 0–1, and R is elected from the group consisting of hydrogen, $C_{1-10}$ alkyl, $C_{1-10}$ aryl and

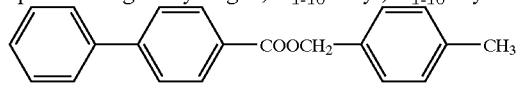

Preferably, the compound to be administered has the following formula III (NE-2001):

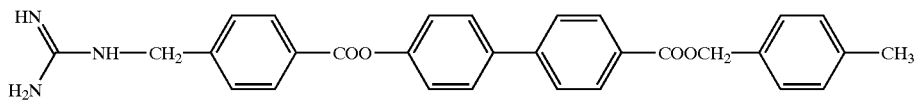

In still another aspect, the present invention is directed to a combination, which combination comprises an agent that selectively inhibits bacterial DNA replication initiation in E. coli or H. pylori, or a pharmaceutically acceptable salt thereof, and an anti-H. pylori or anti-E. coli agent. Preferably, the combination comprises a compound, or a pharmaceutically acceptable salt thereof, having the following formula II:

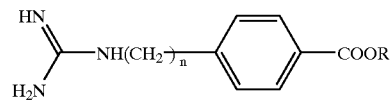

wherein n is an integer from 0–1, and R is elected from the group consisting of hydrogen, $C_{10}$ alkyl, $C_{1-10}$ aryl and

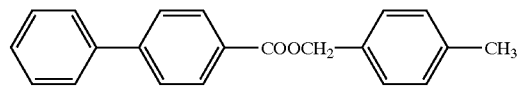

and an anti-H. pylori agent. More preferably, the compound to be included in the combination has the following formula III (NE-2001):

Kits comprising the above combinations are also provided. Methods for treating or preventing a disease or disorder caused by or associated with bacterial infection, e.g., E. coli or H. pylori infection, using the above combinations and kits are further provided.

MODES OF CARRYING OUT THE INVENTION

Figure 1:
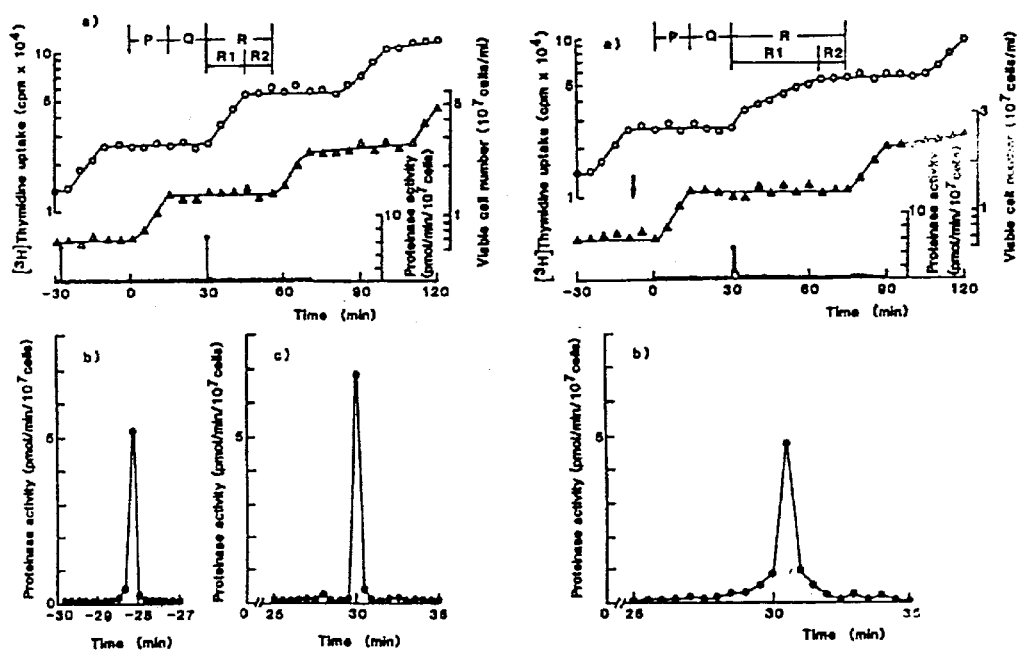
FIG. 1 illustrates effects of the compound PH04 on cell growth, DNA synthesis and proteinase In activity in synchronized E. coli Cells.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, a "Helicobacter" refers to a genus of helical, curved, or straight microaerophilic bacteria with rounded ends and multiple sheathed flagella (unipolar or bipolar and lateral) with terminal bulbs. It forms nonpigmented, translucent colonies, usually 1–2 mm in diameter. It is usually catalase and oxidase positive. It is found in gastric mucosa of primates, including human beings and ferrets. Some species are associated with gastric and peptic ulcers.

As used herein, a "*Helicobacter pylori*" refers to species of the genus of Helicobacter. It is an S-shaped or curved Gram negative bacteria, non-spore forming, and can be flagellate. It is found in human stomach and was originally named *Campylobacter pyloridis*. Infection with *H. pylori* produces urease and is associated with several gastroduodenal diseases including gastritis and gastric, duodenal, and peptic ulcers.

As used herein, "a disease or disorder caused by *H. pylori* infection" refers to a disease or disorder caused by *H. pylori* infection alone or in combination with other agents and/or conditions, whether inheritable and/or acquired.

As used herein, "an anti-*H. pylori* agent" does not encompass the compound of the present invention, i.e., a compound having the following formula II:

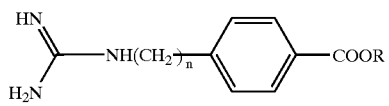

As used herein, a "*Escherichia coli* (*E. coli*)" refers to the archetypal bacterium for biochemists, used very extensively in experimental work. It is a rod-shaped Gram negative bacillus abundant in the large intestine (colon) of mammals. It is normally non-pathogenic; but certain strains, e.g., the *E. coli* O157 strain, common in the intestines of cattle, has recently caused a number of deaths.

As used herein, "a disease or disorder caused by *E. Coli* infection" refers to a disease or disorder caused by *E. coli* infection alone or in combination with other agents and/or conditions, whether inheritable and/or acquired.

As used herein, "an effective amount" of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, "pharmaceutically acceptable salts, esters or other derivatives" include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, "treatment" means any manner in which the symptoms of a condition, disorder or disease are ameliorated or otherwise beneficially altered. Treatment also encompasses any pharmaceutical use of the compositions herein.

As used herein, "amelioration" of the symptoms of a particular disorder by administration of a particular pharmaceutical composition refers to any lessening, whether permanent or temporary, lasting or transient that can be attributed to or associated with administration of the composition.

As used herein, "substantially pure" means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, a "prodrug" is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392).

The term "substantially" identical or homologous or similar varies with the context as understood by those skilled in the relevant art and generally means at least 70%, preferably means at least 80%, more preferably at least 90%, and most preferably at least 95% identity.

As used herein, a "composition" refers to any mixture. It may be a solution, a suspension, liquid, powder, paste, aqueous, non-aqueous or any combination thereof.

As used herein, a "combination" refers to any association between two or among more items.

As employed herein, the term "subject" embraces human as well as other animal species, such as, for example, canine, feline, bovine, porcine, rodent, and the like. It will be understood by the skilled practitioner that the subject is one appropriate to the desirability of treating or preventing diseases or disorders caused by or associated with certain bacterial infection, e.g., *E. coli* or *H. pylori* infection.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

B. Anti-bacterial Agents

The present invention adds to the repertoire of anti-bacteria agents by providing drugs which would inhibit DNA replication initiation in certain bacteria. In one aspect, the present invention is directed to a compound, or a pharmaceutically acceptable salt thereof, having the following formula II:

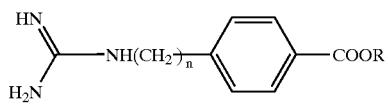

wherein n is an integer from 0–1, and R is elected from the group consisting of hydrogen, a lower alkyl, e.g., $C_{1-10}$ alkyl, a lower aryl, e.g., $C_{1-10}$ aryl and

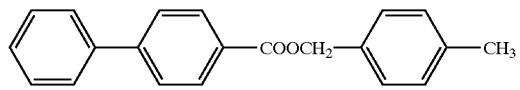

The lower alkyl can be any suitable aliphatic group including alkane, alkene, alkyne and cyclic aliphatic groups. The lower alkyl can be straight carbon-hydrogen groups or can comprise suitable substitutes, e.g., halides. The lower aryl can also be straight carbon-hydrogen groups or can comprise suitable substitutes, e.g., halides.

Preferably, the compound has the following formula III (NE-2001):

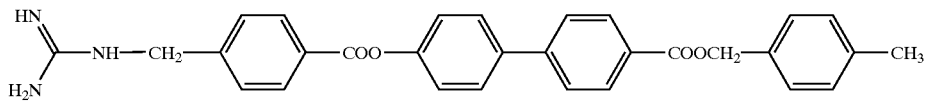

The R group can comprise aromatic groups or esters. Alternatively, the R group does not comprise any aromatic groups or esters.

The compounds of the present invention can be a particular stereoisomer, e.g., R- or S-configuration, or a mixture thereof, e.g., a racemic mixture. The term compounds contemplated herein encompasses all pharmaceutically active species of the compounds, or solutions thereof, or mixtures thereof. The compounds contemplated herein also encompass hydrated versions, such as aqueous solutions, hydrolyzed products or ionized products of these compounds; and these compounds may contain different number of attached water molecules.

The compounds of the present invention can be prepared or synthesized according to any suitable methods. Preferably, synthetic methods illustrated in the following Section F are used to prepare the compounds.

Also preferably, the compound, or its pharmaceutically acceptable salt thereof, is provided in the form of a pharmaceutical composition, either alone or in combination with a pharmaceutically acceptable carrier or excipient.

The compounds of the present invention can be prepared as their pharmaceutically acceptable salts with any suitable acids. For example, inorganic acids, such as hydrochloric acid, hydrobromic acid, nitric acid, sulfuric acid, and phosphoric acid, etc., can be used. In another example, organic acids, such as formic acid, acetic acid, propanoic acid, benzoic acid, maleic acid, fumaric acid, succinic acid, tartaric acid, citric acid, etc., can be used. In still another example, alkyl sulfonic acid, such as methyl sulfonic acid, ethyl sulfonic acid, etc., can be used. In yet another example, aryl sulfonic acid, such as benzene sulfonic acid, p-toluene sulfonic acid, etc, can be used.

C. Treatment and Prevention Methods

In another aspect, the present invention is directed to a method for treating or preventing a disease or disorder caused by or associated with bacterial infection, which method comprises administering, to a subject to which such treatment or prevention is needed or desirable, an effective amount of an agent that selectively inhibits bacterial DNA replication initiation, or a pharmaceutically acceptable salt thereof, thereby said disease or disorder is treated or prevented.

Preferably, the disease or disorder is caused by or associated with *E. coli* or *H. pylori* infection. Also preferably, the disease or disorder caused by or associated with the bacterial, especially, *E. coli* or *H. pylori* infection, is treated or prevented by administering to the subject an effective amount of a compound, or a pharmaceutically acceptable salt thereof, having the following formula II:

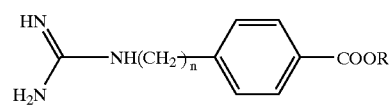

wherein n is an integer from 0–1, and R is elected from the group consisting of hydrogen, $C_{1-10}$ alkyl, $C_{1-10}$ aryl and

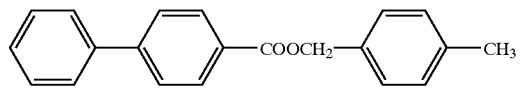

Any suitable compound or its pharmaceutically acceptable salt thereof, including the ones described in the above Section B, can be used. Preferably, the compound to be administered has the following formula III (NE-2001):

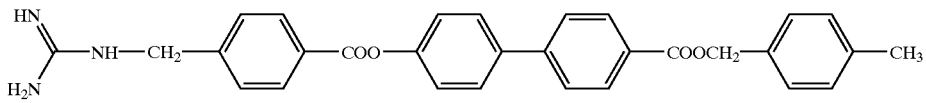

Any subject can be treated by the present method. Preferably, a mammal, and more preferably, a human, is treated by the present method.

The present method can be used to treat or prevent any disease or disorder caused by *E. coli* or *H. pylori* infection. Preferably, the disease or disorder caused by *H. pylori* infection to be treated or prevented is chronic gastritis, gastroduodenal ulcer, adenocarcinoma of the distal stomach, gastric lymphoma or gastric cancer.

The present method can be used to treat or prevent disease or disorder caused by infection of any *E. coli* or *H. pylori* strains. For example, the disease or disorder caused by the following *H. pylori* strains can be treated or prevented:

1: Wang et al., Negative selection of T cells by *Helicobacter pylori* as a model for bacterial strain selection by immune evasion. J Immunol. Jul. 15, 2001; 167(2):926–34.
2: Peek R M Jr., . *Helicobacter pylori* strain-specific activation of signal transduction cascades related to gastric inflammation. J Physiol Gastrointest Liver Physiol. 2001 April; 280(4):G525-30.
3: Israel et al., *Helicobacter pylori* strain-specific differences in genetic content, identified y microarray, influence host inflammatory responses. Clin Invest. 2001 March; 107(5):611–20.
4: Vitkute et al., Specificities of eleven different DNA methyltransferases of *Helicobacter pylori* train 26695. Bacteriol. 2001 January; 183(2):443–50.
5: DeLoney and Schiller, Characterization of an In vitro-selected amoxicillin-resistant strain of *Helicobacter pylori*. Antimicrob Agents Chemother. 2000 December; 44(12):3368–73.
6: Hua et al., Isolation of a single strain of *Helicobacter pylori* from the antrum and body of individual patients. Eur J Gastroenterol Hepatol. 2000 October; 12(10):1129–34.
7: Occhialini et al., Distribution of open reading frames of plasticity region of strain J99 in *Helicobacter pylori* strains isolated from gastric carcinoma and gastritis patients in Costa Rica. Infect Immnun. 2000 November; 68(11):6240–9.
8: Fassbinder et al., Structural and functional analysis of the riboflavin synthesis genes encoding GTP cyclohydrolase II (ribA), DHBP synthase (ribBA), riboflavin synthase (ribC), and riboflavin deaminase/reductase (ribD) from *Helicobacter pylori* strain P1. FEMS Microbiol Lett. Oct., 15, 2000; 191(2):191–7.
9: Enroth et al., *Helicobacter pylori* strain types and risk of gastric cancer: a case-control study. Cancer Epidemiol Biomarkers Prev. 2000 September; 9(9): 981–5.
10: Petersen et al., Role of strain type, AGS cells and fetal calf serum in *Helicobacter pylori* adhesion and invasion assays. FEMS Immunol Med Microbiol. 2000 September; 29(1):59–67.
11: Matsui et al., Recurrence of gastric ulcer dependent upon strain differences of *Helicobacter pylori* in urease B gene. Dig Dis Sci. 2000 January; 45(1):49–54.
12: Queiroz et al., Factors associated with *Helicobacter pylori* infection by a cagA-positive strain in children. J Infect Dis. 2000 February; 181(2):626–30.
13: Monteiro et al., Lipopolysaccharide structures of *Helicobacter pylori* genomic strains 26695 and J99, mouse model *H. pylori* Sydney strain, *H. pylori* P466 carrying sialyl Lewis X, and *H. pylori* UA915 expressing Lewis B classification of *H. pylori* lipopolysaccharides into glycotype families. Eur J Biochem. 2000 January; 267(2):305–20.
14: Peek et al., *Helicobacter pylori* strain-specific genotypes and modulation of the gastric epithelial cell cycle. Cancer Res. Dec 15, 1999; 59(24):6124–31.
15: Aspinall et al., A structural comparison of lipopolysaccharides from two strains of *Helicobacter pylori*, of which one strain (442) does and the other strain (471) does not stimulate pepsinogen secretion. Glycobiology. 1999 November; 9(11):1235–45.
16: Enroth et al., Occurrence of resistance mutation and clonal expansion in *Helicobacter pylori* multiple-strain infection: a potential risk in clarithromycin-based therapy. Clin Infect Dis. 1999 June; 28(6):1305–7.
17: Hua et al., Predominance of a single strain of *Helicobacter pylori* in gastric antrum. Helicobacter. 1999 March; 4(1):28–32.
18: van Doom et al., *Helicobacter pylori*-associated gastritis in mice is host and strain specific. Infect Immun. 1999 June; 67(6):3040–6.
19: van Doom et al., The inflammatory response in CD1 mice shortly after infection with a CagA+/VacA+ *Helicobacter pylori* strain. Clin Exp Immunol. 1999 March;115(3):421–7.
20: De Ungria et al., Molecular characterization and interstrain variability of pHPS 1, a plasmid isolated from the Sydney strain (SS 1) of *Helicobacter pylori*. Plasmid. 1999 March; 41(2):97–109.

In treating or preventing a disease or disorder caused by *H. pylori* infection, the compounds of the present invention can be used alone or can be used in combination with an anti-*H. pylori* agent. Any suitable anti-*H. pylori* agent can be used in combination with the compounds of the present invention. Such exemplary anti-*H. pylori* agents include proton-pump inhibitor (PPI), metronidazole, clarithromycin, amoxicillin and famotidine (Gaschwantler et al., *Eur. J. Gastroenterol Hepatol.*, 10(7):579–82 (1998)).

In a preferred embodiment, the compounds of the present invention are used without administering an anti-*H. pylori* agent such as PPI, metronidazole, clarithromycin, amoxicillin and famotidine. More preferably, the compounds of the present invention are used to treat or prevent diseases or disorders caused by a *H. pylori* resistant strain induced by PPI, metronidazole, clarithromycin amoxicillin or famotidine treatment.

The compounds of the present invention, alone or in combination with other suitable anti-*H. pylori* agents, can be administered by any suitable methods. For example, the compound or a pharmaceutically acceptable salt thereof of the present invention can be administered by intracavernous injection, subcutaneous injection, intravenous injection, intramuscular injection, intradermal injection, oral administration, or topical administration.

In a specific embodiment, the present method further comprises a step of diagnosing or pragnosing *H. pylori* infection in the subject. Any suitable method for diagnosing or pragnosing H. pylori infection can be used. The prognosis or diagnosis can be based upon the detection and/or identification of any or all H. pylori protein(s) such as its enzymes, antigens and antibodies, nucleic acid(s), or other pathological or clinical markers and symptoms. For example, the diagnosing or pragnosing methods disclosed in WO 01/44815 and U.S. Pat. No. 5,571,674 can be used.

D. Combinations, Kits and Combinatorial Methods

In still another aspect, the present invention is directed to a combination, which combination comprises an agent that selectively inhibits DNA replication initiation in E. coli or H. pylori, or a pharmaceutically acceptable salt thereof, and an anti-H. pylori or anti-E. coli agent.

Preferably, the combination comprises a compound, or a pharmaceutically acceptable salt thereof, having the following formula II:

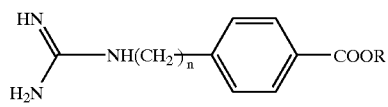

wherein n is an integer from 0–1, and R is elected from the group consisting of hydrogen, $C_{1-10}$ alkyl, $C_{1-10}$ aryl and

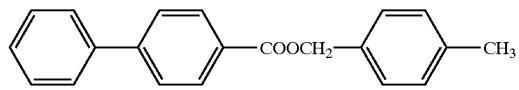

and an anti-H. pylori agent. More preferably, the compound to be included in the combination has the following formula III (Ne-2001):

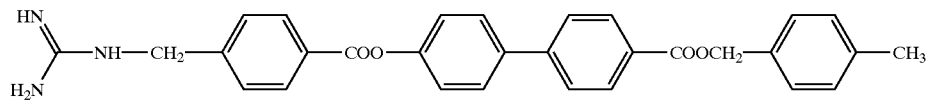

Any suitable anti-H. pylori agent can be used in the present combination. In a specific embodiment, the anti-H. pylori agent used in the combination is PPI, metronidazole, clarithromycin, amoxicillin or famotidine.

In another specific embodiment, a method for treating or preventing a disease or disorder caused by bacterial infection, e.g., E. coli or H. pylori infection, is provided, which method comprises administering, to a subject to which such treatment or prevention is needed or desirable, an effective amount of the above combination, or a pharmaceutically acceptable salt thereof, thereby said disease or disorder is treated or prevented.

In yet another specific embodiment, a kit is provided, which kit comprises the compound of the present invention, or a pharmaceutically acceptable salt thereof, and an instruction for using said compound or pharmaceutically acceptable salt in treating or preventing a disease or disorder caused by a bacterial infection, e.g., E. coli or H. pylori infection.

In yet specific embodiment, a kit is provided, which kit comprises the above combination, and an instruction for using said combination in treating or preventing a disease or disorder caused by a bacterial infection, e.g., E. coli or H. pylori infection.

E. Formulations and Dosages

According to the present invention, the compounds of the present invention, alone or in combination with other agents, carriers or excipients, may be formulated for any suitable administration route, such as intracavernous injection, subcutaneous injection, intravenous injection, intramuscular injection, intradermal injection, oral or topical administration. The method may employ formulations for injectable administration in unit dosage form, in ampoules or in multidose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogen-free water or other solvents, before use. Topical administration in the present invention may employ the use of a foam, gel, cream, ointment, transdermal patch, or paste.

Pharmaceutically acceptable compositions and methods for their administration that may be employ for use in this invention include, but are not limited to those described in U.S. Pat. Nos. 5,736,154; 6,197,801 B1; 5,741,511; 5,886,039; 5,941,868; 6,258,374 B1; and 5,686,102.

The magnitude of a therapeutic dose in the treatment or prevention will vary with the severity of the condition to be treated and the route of administration. The dose, and perhaps dose frequency, will also vary according to age, body weight, condition and response of the individual patient.

It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

Any suitable route of administration may be used. Dosage forms include tablets, troches, cachet, dispersions, suspensions, solutions, capsules, patches, and the like. See, Remington's Pharmaceutical Sciences.

In practical use, the compounds of the present invention, alone or in combination with other agents, may be combined as the active in intimate admixture with a pharmaceutical carrier or excipient, such as beta-cyclodextrin and 2-hydroxy-propyl-beta-cyclodextrin, according to conventional pharmaceutical compounding techniques. The carrier may take a wide form of preparation desired for administration, topical or parenteral. In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of the compounds of the present invention, alone or in combination with other agents to be administered may be administered in a vial of intravenous fluid, ranging from about 1 ml to 2000 ml. The volume of dilution fluid will vary according to the total dose administered.

The invention also provides for kits for carrying out the therapeutic regimens of the invention. Such kits comprise in one or more containers therapeutically effective amounts of the compounds of the present invention, alone or in combination with other agents, in pharmaceutically acceptable form. Preferred pharmaceutical forms would be in combination with sterile saline, dextrose solution, or buffered solution, or other pharmaceutically acceptable sterile fluid. Alternatively, the composition may be lyophilized or dessicated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In another embodiment, a kit of the invention further comprises a needle or syringe, preferably packaged in sterile form, for injecting the composition, and/or a packaged alcohol pad. Instructions are optionally included for administration of composition by a physician or by the patient.

F. EXAMPLES

Example 1

Synthesis of a Series of Novel Anti-*H. pylori* Compounds

Since its discovery in 1983, in the mucus linings of the stomachs of patients with chronic gastritis, scientists have made detailed studies of *H. pylori*. Strong evidence exists to support the hypothesis that *H. pylori* may cause ulcers in the stomach and duodenum.

*H. pylori* infects approximately 60% of people throughout the world and is the most common gastrointestinal infection worldwide. Some people develop gastritis, peptic ulcers and even gastric cancer as a result of infection. As it is a spiral shaped, thickly coated bacteria, with several flagellaes in its outer surface, it is very well adapted to the microenvironment of the upper gastrointestinal (GI) tract and hard to be eradicated.

Here we are aiming to synthesize series compounds, and have found that NE-2001

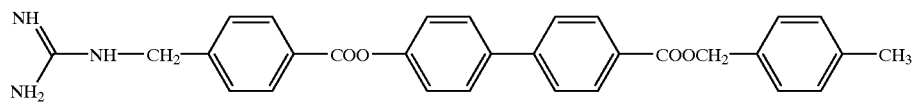

has specific and selective actions on *H. pylori*, and thus can be used in more cost-effective methods of multi-drug therapies.

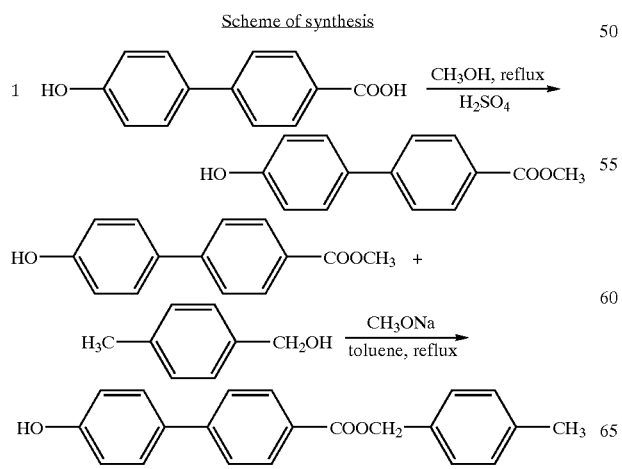

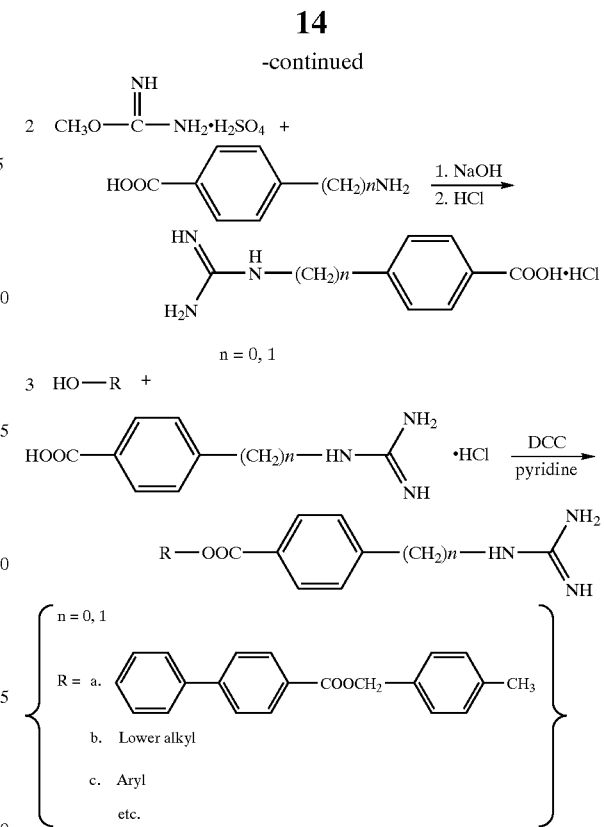

Experimental Section

Instruments and Reagents

HP 1100 HPLC system, including binary pump, on-line degasser, auto-sampler, thermostatted column compartment, diode-array detector. The column is ZORBAX ODS (4.6*250 mm). Mobile phase is methanol/water=90:10 (0.1% acetic acid). Flow rate is 1 mL/min. The detector wave is 254 nm.

All solvents are HPLC grade. MS spectra are obtained by API 2000 LC/MS/MS system. $^1$H-NMR data are from Analysis Center of East China University of Science and Technology. All starting materials are publicly available in the market.

Synthesis of 4-(4-Methylbenzyl)-4'-hydroxybiphenyl-4-carboxylate 4-Methyl-4'-hydroxybiphenyl-4-carboxylate A solution of 4-(4-hydroxyphenyl) benzoic acid 21.4 g (0.1 mol) in 500 mL absolute methanol in a flask equipped Soxhlet apparatus filled with A4 molecular sieve. Then dropped 2.0 mL concentrated sulfuric acid. The mixture refluxed for 72 hrs. After removal the solvent by vacuum, the residual oil dissolved in 100 mL toluene, washed to pH=7 with water. The organic layer was dried by $MgSO_4$ and filtered. The obtained filter liquor was added a certain quantity of activated charcoal and heated to reflux for 10~15 min and filtered. Removed the solvent to obtain a white crystal, 4-Methyl-4'-hydroxybiphenyl-4-carboxylate 18.2 g (yield 80%).

4-(4-Methylbenzyl)-4'-hydroxybiphenyl-4-carboxylate

A suspension of 4-Methyl-4-hydroxybiphenyl-4-carboxylate 9.0 g (40.0 mmol), 4-methylbenzylalcohol 24.4 g (200.0 mmol), sodium methoxide 1.0 g (4.0 mmol), toluene 20.0 mL, under $N_2$ prevention, was heated to reflux 2.5 hrs. During the reaction, added additional 20.0 mL toluene in order to bring out the resultant methanol under reflux. Then cooled to room temperature, added 10 mL acetic acid and ice 40 g to adjust the pH=5. The obtained organic layer was concentrated under reduced pressure to remove solvent and the excess 4-methylbenzylalcohol. Cooled to obtain brownish oil. Stood to produce the crude crystals slowly. Recrystallized from toluene/n-hexane to give a white crystal, 4-(4-methylbenzyl)-4'-hydroxybiphenyl-4-carboxylate 7.3 g (yield 71%).

$^1$H-NMR(500 MHz,CDCl$_3$): δ2.35(s, 3H), 5.35(s, 2H), 6.90(d, 2H), 7.15(d, 2H), 7.35(d, 2H), 7.50(d, 2H), 7.60(d, 2H), 8.10(d, 2H)

Synthesis of 4-guanidinoalkylbenzoic acid hydrochloride 4-Guanidinomethyl benzoic acid hydrochloride 2N NaOH solution 72 mL was added to a solution of methyl isothiourea disulfate 20.0 g (0.14 mol) in 36 mL water with cooling in ice bath, and stirred. Then 21.0 g (0.138 mol) 4-aminomethylbenzoic acid in 140 mL 2N NaOH solution was added dropwise. The mixture was left to stand overnight at room temperature and then chilled in ice water for 1 hr. The precipitated white crystals were filtered off and washed with cold water. The filtrate was dissolve in warm 1N HCl and insoluble material was removed by filtration. The solution was concentrated in vacuum to crystallize. The colorless prisms crystallized when the solution was cooled, then filtered and dried, gave 4-guanidinomethylbenzoic acid hydrochloride 22.1 g(yield 70%).

LC/MS=194(M+H)

4-Guanidino benzoic acid hydrochloride

2N NaOH solution 36 mL was added to a solution of methyl isothiourea disulfate 10.0 g (0.07 mol) in 36 mL water with cooling in ice bath, and stirred, then 9.5 g (0.069 mol) 4-aminomethylbenzoic acid in 2N NaOH solution 70 mL was added dropwise. The mixture was left to stand overnight at room temperature and then chilled in ice water for 1 hr. The precipitated white crystals were filtered off and washed with cold water. The filtrate was dissolve in warm 1N HCl and insoluble material was removed by filtration. The solution was concentrated in vacuum to crystallize. The colorless prisms crystallized when the solution was cooled, then filtered and dried, gave 4-guanidinobenzoic acid hydrochloride 10.0 g (yield 67%).

LC/MS=180(M+H)

Synthesis of 4-guanidinoalkyl benzoate 4-(4-methylbenzyl)-4'-[guanidinomethylbenzoyloxy] biphenyl-4-carboxylate hydrochloride A suspension of 4-methylbenzyl-4'-hydroxybiphenyl-4-carboxylate, 2.42 g(0.010 mol), 4-Guanidinomethyl benzoic acid hydrochloride 2.3 g (0.010 mol) and dicyclohexylcabodiimide 4.1 g(0.020 mol) in pyridine 150 ml was stirred at room temperature for 48 hrs, after removed of insoluble materials by filtration. The filtrate was evaporated to dryness and residue solid was treated with 0.1N hydrochloric acid (50 mL) and ether (50 mL), The aqueous layer was washed with ether again and concentrated to 20 ml, the resulting crystals were recrystallized in ethanol/hexane, gave 4-(4-methylbenzyl)-4'[guanidinomethylbenzoyloxy] biphenyl-4-carboxylate Hydrochloride 2.9 g (yield 55%).

LC/MS=494(M+H)

4-(4-methylbenzyl)-4'-[guanidinobenzoyloxy] biphenyl-4-carboxylate hydrochloride A suspension of 4-methylbenzyl-4'-hydroxybiphenyl-4-carboxylate, 2.42 g(0.010 mol), 4-Guanidinobenzoic acid hydrochloride 2.2 g (0.010 mol) and dicyclohexylcabodiimide 4.1 g(0.020 mol) in pyridine 150 ml was stirred at room temperature for 48 hrs, after removed of insoluble materials by filtration. The filtrate was evaporated to dryness and residue solid was treated with 0.1N hydrochloric acid (50 mL) and ether (50 mL), The aqueous layer was washed with ether again and concentrated to 20 ml, the resulting crystals were recrystallized in ethanol/hexane, gave 4-(4-methylbenzyl)-4'-[guanidinobenzoyloxy] biphenyl-4-carboxylate Hydrochloride 3.0 g(yield 60%).

LC/MS=482(M+H)

4-Phenyl-4'-guanidinomethylbenzoate hydrochloride

A suspension of 4-guanidinomethylbenzoic acid hydrochloride 2.3 g (0.010 mol), phenol 1.0 g (0.011 mol) and dicyclohexylcarbodimide 4.1 g (0.020 mol) in pyridine (150 ml) was stirred at room temperature for 48 hrs. After removal of insoluble materials by filtration, the filtrate was evaporated to dryness and residual solid was treated with 0.1N hydrochloric acid (50 ml),washed with ether. The aqueous layer was concentrated to 20 ml, the resulting crystals were filtered and washed with isopropanol/isopropyl ether, gave 4-Phenyl-4'-guanidinomethylbenzoate hydrochloride 2.3 g (yield 75%).

LC/MS=269(M+H)

4-Phenyl-4'-guanidinobenzoate hydrochloride

A suspension of 4-guanidinobenzoic acid hydrochloride 2.2 g (0.010 mol), phenol 1.0 g (0.011 mol) and dicyclohexylcarbodimide 4.1 g (0.020 mol) in pyridine (150 ml) was stirred at room temperature for 48 hrs. After removal of insoluble materials by filtration, the filtrate was evaporated to dryness and residual solid was treated with 0.1N hydrochloric acid (50 ml), washed with ether. The aqueous layer was concentrated to 20 ml, the resulting crystals were filtered and washed with isopropanol/isopropyl ether, gave 4-Phenyl-4'-guanidinobenzoate hydrochloride 2.2 g (yield 75%).

LC/MS=255(M+H)

4-(4-Biphenyl)-4'-guanidinomethylbenzoate hydrochloride

A suspension of 4-guanidinomethylbenzoic acid hydrochloride 2.3 g(0.01 mol), 4-phenylphenol 1.7 g (0.010 mol) and dicyclohexylcarbodimide 4.1 g (0.020 mol) in pyridine (150 ml) was stirred at room temperature for 48 hrs. After removal of insoluble materials by filtration, the filtrate was evaporated to dryness and residual solid was treated with 0.1N hydrochloric acid (50 ml), washed with ether. The aqueous layer was concentrated to 20 ml, the resulting crystals were filtered and washed with isopropanol/ isopropyl ether, gave 4-(4-biphenyl)-4'-guanidinomethylbenzoate hydrochloride 2.5 g (yield 65%).

LC/MS=346 (M+H)

4-(4-Biphenyl)-4'-guanidinobenzoate hydrochloride

A suspension of 4-guanidinobenzoic acid hydrochloride 2.2 g(0.010 mol), 4-phenylphenol 1.7 g (0.010 mol) and dicyclohexylcarbodimide 4.1 g (0.020 mol) in pyridine (150 ml) was stirred at room temperature for 48 hrs. After removal of insoluble materials by filtration, the filtrate was evaporated to dryness and residual solid was treated with 0.1N hydrochloric acid (50 ml), washed with ether. The aqueous layer was concentrated to 20 ml, the resulting crystals were filtered and washed with isopropanol/ isopropyl ether, gave 4-(4-biphenyl)-4'-guanidinobenzoate hydrochloride 2.6 g (yield 70%).

LC/MS=332 (M+H)

4-(4-Methylphenyl)-4'-guanidinomethylbenzoate hydrochloride

A suspension of 4-guanidinomethylbenzoic acid hydrochloride 2.3 g (0.010 mol), 4-methylphenol 1.1 g (0.010 mol) and dicyclohexyl-carbodimide 4.1 g (0.020 mol) in pyridine (150 ml) was stirred at room temperature for 48 hrs. After removal of insoluble materials by filtration, the filtrate was evaporated to dryness and residual solid was treated with 0.1N hydrochloric acid (50 ml), washed with ether. The aqueous layer was concentrated to 20 ml, the resulting crystals were filtered and washed with isopropanol/ isopropyl ether, gave 4-(4-methylphenyl)-4'-guanidinomethylbenzoate hydrochloride 2.4 g (yield 75%).

LC/MS=284 (M+H)

4-(4-Methylphenyl)-4'-guanidinobenzoate hydrochloride

A suspension of 4-guanidinobenzoic acid hydrochloride 2.2 g(0.010 mol), 4-methylphenol 1.1 g (0.010 mol) and dicyclohexyl-carbodimide 4.1 g (0.020 mol) in pyridine (150 ml) was stirred at room temperature for 48 hrs. After removal of insoluble materials by filtration, the filtrate was evaporated to dryness and residual solid was treated with 0.1N hydrochloric acid (50 ml), washed with ether. The aqueous layer was concentrated to 20 ml, the resulting crystals were filtered and washed with isopropanol/ isopropyl ether, gave 4-(4-methylphenyl)-4'-guanidinobenzoate hydrochloride 2.2 g (yield 75%).

LC/MS=270 (M+H)

References and Notes

1. U.S. Pat. No. 4, 348,410
2. J.O.C. vol. 33 (1985) 652
3. Wenren et al Reactions of drugs synthesis published by chemical industry of China.
4. Chen fener et al Synthesis methods of organic drug published by Pharmaceutical science technology of China Example 2

Activities of GMCHA Derivatives

Different modifications of GMCHA were found to have differing inhibitory effects on the growth of *E. coli* (Table 1). For example, while the phenyl ester (PH01) derivative had an $IC_{50}$ of >200 μM on *E. coli* growth, various modifications at the 4-methylpheny (PH02), 4-ethylphenyl (PH03), 4-tert-butylphenyl (PH04), and 4-biphenyl (BP01) decreased from>200, to 167, to 45, and to 26 μM, respectively. Significantly, the effects of these compounds were not restricted to *E. coli*. (Irisawa et al., *Biol. Pharm. Bull.*, 16:1211–1215 (1993); and Kato et al., *J. Enzyme Inhibition*, 8:25–37 (1994)). The relative effects of individual members of this class of molecules remained the same whether the target cells were *E.coli, B. Subtilis, S. aureus* or *S. epidermidis* (Table 2). In each case, the most effective compound remained the 4-biphenyl (BP01) derivative. Interestingly, the $IC_{50}$ for a specific compound varied significantly for different bacterial species, with almost a two-log difference between those that were tested. For the 4-biphenyl ester (BP01), for example, it seemed that Staphylococcus was one log more sensitive than Bacillus, which was in turn one log more sensitive than Escherichia.

TABLE 1

Effects of GMCHA derivatives on *E. coli* Growth and Proteinase In Activity

| COMPOUND | STRUCTURE | *E. coli* Growth $IC_{50}$ (μM) | *E. coli* Proteinase In $IC_{50}$ (μM) | Trypsin $K_i$ (μM) |
| --- | --- | --- | --- | --- |
| PH01 Phenyl | O—⟨phenyl⟩ | >200 | >200 | 110 |
| PH02 4-Methylphenyl | O—⟨phenyl⟩—CH₃ | >200 | >200 | 78 |
| PH03 4-Ethylphenyl | O—⟨phenyl⟩—CH₂—CH₃ | 167 | >200 | 48 |

TABLE 1-continued

Effects of GMCHA derivatives on *E. coli* Growth and Proteinase In Activity

| COMPOUND | | STRUCTURE | *E. coli* Growth IC$_{50}$ ($\mu$M) | *E. coli* Proteinase In IC$_{50}$ ($\mu$M) | Trypsin K$_i$ ($\mu$M) |
|---|---|---|---|---|---|
| PH04 | 4-tert-Butylphenyl | O—⟨phenyl⟩—C(CH$_3$)$_3$ | 45 | 38 | 64 |
| PH05 | 2,4-Dichlorophenyl | Cl, O—⟨phenyl⟩—Cl | 92 | 62 | 46 |
| PH06 | 2,4,6-Trichlorophenyl | Cl, O—⟨phenyl⟩—Cl, Cl | 44 | 35 | 273 |
| BP01 | 4-Biphenyl | O—⟨phenyl⟩—⟨phenyl⟩ | 26 | 17 | 54 |
| BP02 | 2-Biphenyl | O—⟨phenyl⟩(−⟨phenyl⟩) | 74 | 83 | 187 |

TABLE 2

Effects of Various Aromatic Esters of GMCHA on the Growth of Different Bacterial Species

| COMPOUND | | STRUCTURE | *E. coli* | | *B. subtilis* | | *S. aureus* | | *S. epidermidis* | |
|---|---|---|---|---|---|---|---|---|---|---|
| | | | IC$_{91}$ | IC$_{100}$ | IC$_{50}$ | IC$_{100}$ | IC$_{20}$ | IC$_{100}$ | IC$_{91}$ | IC$_{100}$ |
| PH01 | Phenyl | O—⟨phenyl⟩ | >200 | >200 | >200 | >200 | 151 | >200 | 128 | >200 |
| PH02 | 4-Methylphenyl | O—⟨phenyl⟩—CH$_3$ | >200 | >200 | >200 | >200 | 47 | 120 | 48 | 120 |
| PH03 | 4-Ethylphenyl | O—⟨phenyl⟩—CH$_2$—CH$_3$ | 167 | >200 | 129 | >200 | 15 | 50 | 14 | 50 |
| PH04 | 4-tert-Butylphenyl | O—⟨phenyl⟩—C(CH$_3$)$_3$ | 45 | 90 | 26 | 50 | 3.4 | 15 | 2.9 | 10 |
| BP01 | 4-Biphenyl | O—⟨phenyl⟩—⟨phenyl⟩ | 26 | 40 | 4 | 10 | 0.6 | 2 | 0.4 | 1.5 |

FIG. 1 illustrates the effects of GMCHA derivatives on cell growth, DNA synthesis and proteinase In activity in synchronized *E. coli* Cells. Left, Growth of synchronized cells in the absence of compound PH04. (a), Viable cell number and [$^3$H] thymidine uptake were determined at 5-min intervals, and proteinase In activity was determined at 30-sec intervals. Time zero was set at the first sign of cell division. (b) and (c), Appearance of proteinase In activity at −30 min and +30 min, respectively. P, Q, and R represent the cell division period, the period between cell division and initiation of chromosome replication, and the period between initiation of chromosome replication and cell division, respectively. Right, Growth of synchronized cells in the presence of 27 μM compound PH04. (a), The inhibitor was added at −8 min (arrow). The sample was as described above. Note that without PHO4, duration of P, Q, R1, and R2 was 15, 15, 15, and 10 min, respectively, whereas with PH04, DNA synthesis was initiated at 30 min and DNA synthetic activity doubled at 65 min. The R1 period was prolonged from 15 to 35 min. (b), Appearance of proteinase activity at about 30 min as in control cells, but had a prolonged half-life.

Figure 2:
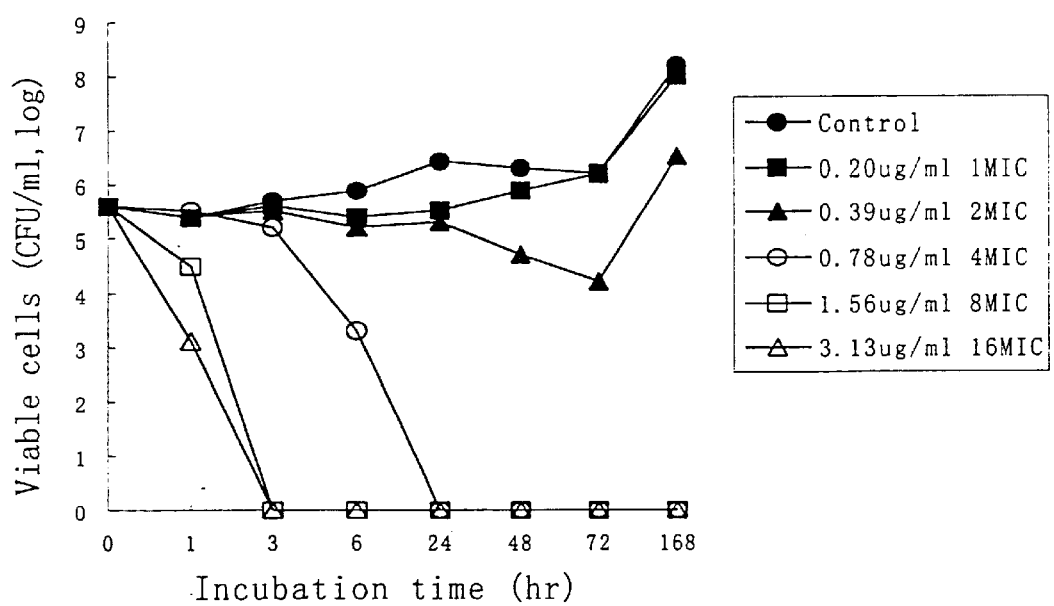
FIG. 2 illustrates the anti-H. pylori effects of the compound NE-2001.-

Since the GMCHA derivatives were originally identified as synthetic trypsin inhibitors in vitro, we investigated whether a trypsin-like protease could be detected in *E. coli* extracts using as fluorogenic substrate Boc-Val-Pro-Arg-NH-Mec. (Kato et al., *Eur. J. Biochem.*, 210:1007–1014 (1992)). We detected a single activity and had purified it to homogeneity. This was achieved in eight steps, with a 2,880-fold purification and a yield of 15 percent. The purified enzyme has a molecular mass of ~66 kDa and an isoelectric point of 4.9. Based upon pH optimum, hydrolytic activity on various synthetic substrates, and effects of various known proteolytic inhibitors, this *E. coli* protease has very different specificity than mammalian trypsin or any of known bacterial enzymes. Most exciting is the finding that the sensitivity of the purified enzyme to various GMCHA derivatives paralleled exactly their inhibitory effects on *E. coli* (Table 1). This latter finding may suggest that this protease is the molecular target within the *E. coli* cell for this class of growth inhibitory compounds. We had gone on to demonstrate, using synchronized *E. coli* cultures, that expression of this protease is restricted to just before the initiation of chromosomal DNA replication (FIG. 2, left). (Kato et al., *Biol.Pharm. Bull.*, 16:552–557 (1993)). Furthermore, addition of the 4-tert-butylphenyl (PH04) derivative after DNA synthesis had initiated did not affect that round of cell division but retarded the next cycle. However, addition of the inhibitor prior to the initiation of DNA replication resulted in prolongation of that same round of cell division (FIG. 1, right). Together, these results suggest that this protease probably participates directly in the initiation of chromosome replication in *E. coli*, and that it is the target of inhibition by the aromatic esters of GMCHA. We named this enzyme proteinase In, and its gene was identical with prlC. The prlC gene encoded a 67 kDa protein with two active sites for proteinase In and oligopeptidase A. (Jiang et al., *J. Biochem.*, 124:980–985 (1998)). A proteinase In like proteinase was partially purified from *B. Subtilis* and it was stonily inhibited by various esters of GMCHA, and their effects were co-related with their inhibitory effects on the growth of the bacteria. (Irisawa et al., *Biol. Pharm. Bull.*, 16:1211–1215 (1993)). These results strongly suggest the ubiquitous occurrence of proteinase In or proteinase In-like proteinase in various bacteria, and a strong inhibitor for the proteinase is useful as an new type of antibacterial agent.

Example 3

Activities of NE-2001

A novel compound reported here 4-(4-methylbenzyl)-4'-[guanidinomethylbenzoyloxy] biphenyl-4-carboxylate, NE-2001, specifically inhibited the growth of *H. pylori* and completely eradicated *H. pylori* at various pH.

MICs (μg/ml) of several substances against 9 strains (ATCC43504, ATCC43629, ATCC43526, ATCC43579, ATCC49503, ATCC51110, ATCC51652, ATCC51653, ATCC51932) of *H. pylori* were examined. NE-2001 had minimal inhibitory concentrations (MICs) ranging from 0.10 to 0.48 μg/ml. Summary is shown in the following Table 3.

TABLE 3

Summary of MIC Range against *H. pylori*

| Substance | MIC Range (μg/ml) |
|---|---|
| NE-2001 | 0.10–0.48 |
| Amoxicillin | 0.01–0.08 |
| Clarithromycin | 0.01–0.90 |
| Metronidazole | 0.65–2.45 |

FIG. 2 illustrates the anti-*H. pylori* effects of the compound NE-2001. Bactericidal effect was examined at various concentration (0.15–2.50 μg/ml) for 168 hours. The representative curve was shown in FIG. 2. NE-2001 showed strong bactericidal effect against *H. pylori*. No visible organism was detected in 3 hr at a concentration of ≧1.25 μg/ml. NE-2001 showed bactericidal effect against *H. pylori* in all tested pH range (pH3–7) (See FIG. 3).

Figure 3:
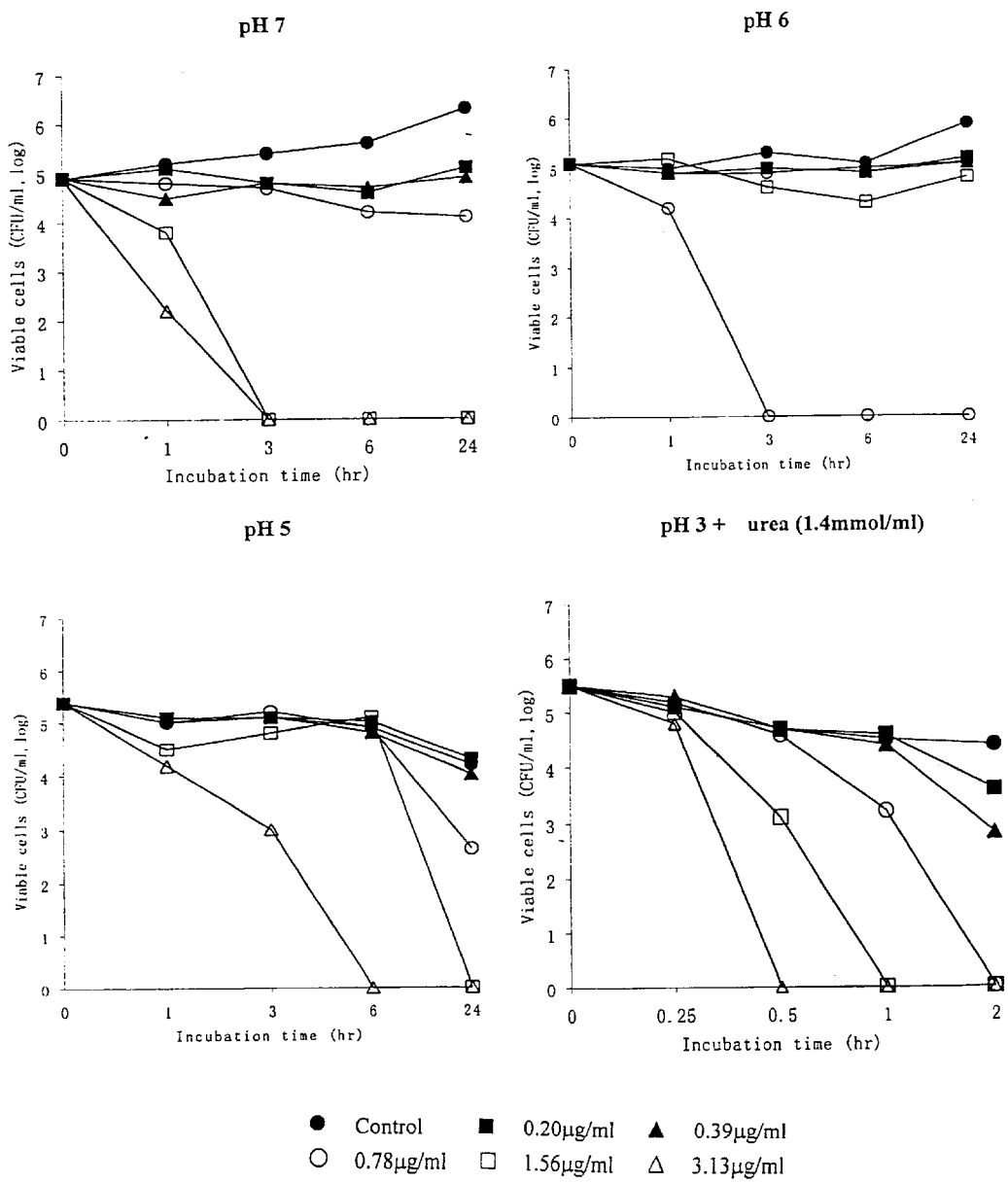
FIG. 3 illustrates the anti-H. pylori effects of the compound NE-2001 at various pH values.

FIG. 3. Illustrates the anti-*H. pylori* effects of the compound NE-2001 at various pH values. The appearance frequency of natural resistant mutations against NE-2001 was examined (Table 4). Obviously no natural resistant bacteria appeared at all tested concentration of NE-2001 (0.30–1.20, μg/ml).

TABLE 4

Appearance Frequency of Natural Resistant Mutation against NE-2001

| Organism | Selected Concentration Of NE-2001 (μg/ml) | Frequency |
|---|---|---|
| *H. pylori* | 0.30 | <3.4 × 10$^{-8}$ |
| ATCC43504 | 0.60 | <3.4 × 10$^{-8}$ |
|  | 1.20 | <3.4 × 10$^{-8}$ |

A study on a single dose toxicity of NE-2001 was performed orally in male mice. At a dose of 2000 mg/kg of NE-2001 (maximum dose prepared as 0.5% methylcellulose suspension), no animal deaths occurred and all animals gained weight. General toxicity was also observed in neither cases. Apparently, NE-2001 is a safe (Table 5).

TABLE 5

NE-2001 Single Dose Toxicity in Mice

| Animal/Age | Mouse/6 Weeks |
|---|---|
| Administration Route | Oral |
| Sex | Male |
| No. Of Animals/Group | 5 |
| LD$_{50}$ (mg/kg) | >2000 |

The above examples are included for illustrative purposes only and is not intended to limit the scope of the invention. Since modifications will be apparent to those of skill in this art, it is intended that this invention be limited only by the scope of the appended claims.

What is claimed is:

1. A method for treating or preventing *Helicobacter pylori* (*H. pylori*) infection in a subject, which method comprises administering, to a subject for which such treatment or prevention is needed or desirable, an effective amount of a compound having the following formula I:

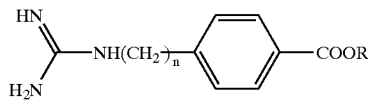

wherein n is 0 or 1, and R is selected from the group consisting of $C_{1-10}$ alkyl, $C_{6-10}$ aryl and

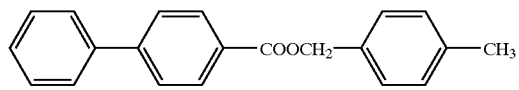

and wherein when n is 0, R, is not $C_{6-10}$ aryl, or a pharmaceutically acceptable salt thereof, thereby said infection is treated or prevented.

2. The method of claim 1, wherein the subject is a mammal.

3. The method of claim 2, wherein the mammal is a human.

4. The method of claim 1, which comprises administering a compound having the following formula II:

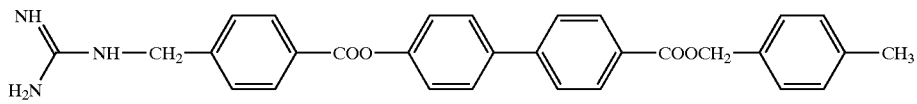

or a pharmaceutically acceptable salt thereof, to the subject.

5. The method of claim 1, which comprises administering a pharmaceutical composition comprising a compound, or a pharmaceutically acceptable salt thereof, having the following formula I:

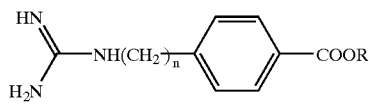

wherein n is 0 or 1, and R is selected from the group consisting of $C_{1-10}$ alkyl, $C_{6-10}$ aryl and

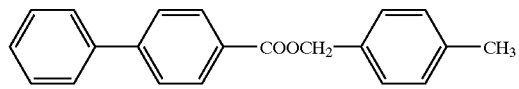

and wherein when n is 0, R, is not $C_{6-10}$ aryl, to the subject.

6. The method of claim 1, wherein a disease or disorder caused by *H. pylori* infection to be treated or prevented is chronic gastritis, gastroduodenal ulcer, adenocarcinoma of the distal stomach, gastric lymphoma or gastric cancer.

7. The method of claim 1, wherein the subject is treated without administering an anti-*H pylori* agent.

8. The method of claim 7, wherein the anti-*H. pylori* agent is a proton-pump inhibitor (PPI), metronidazole, clarithromycin or amoxicillin.

9. The method of claim 1, wherein the *H. pylori* is a resistant strain induced by PPI, metronidazole, clarithromycin or amoxicillin treatment.

10. The method of claim 1, wherein the compound or a pharmaceutically acceptable salt thereof is administered by intracavernous injection, subcutaneous injection, intravenous injection, intramuscular injection, intradermal injection, oral administration, or topical administration.

11. The method of claim 1, which further comprises a step of diagnosis or prognosis of *H. pylori* infection in the subject.

12. A composition, which composition comprises a compound having the following formula I:

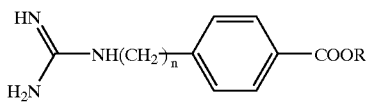

wherein n is 0 or 1, and P. is selected from the group consisting of $C_{1-10}$ alkyl. $C_{6-10}$ aryl and

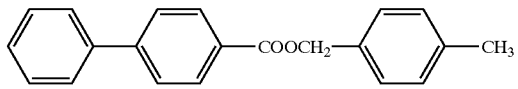

and wherein when n is 0, R, is not $C_{6-10}$ aryl, or a pharmaceutically acceptable salt thereof, and an anti-*H. pylori* agent.

13. The composition of claim 12, wherein the anti-*H. pylori* agent is PPI, metronidazole, clarithromycin or amoxicillin.

14. A method for treating or preventing *H. pylori* infection in a subject, which method comprises administering, to a subject to for which such treatment or prevention is needed or desirable, an effective amount of the composition of claim 12, or a pharmaceutically acceptable salt thereof, thereby said infection is treated or prevented.

15. A kit, which kit comprises the composition of claim 12, and an instruction for using said composition in treating or preventing *H. pylori* infection in a subject.

16. A compound, which has the following formula II:

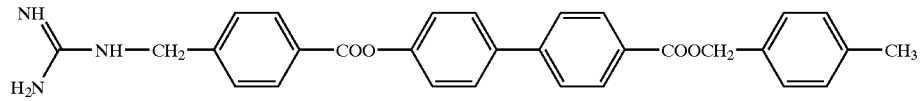

or a pharmaceutically acceptable salt thereof.

17. A pharmaceutical composition, which composition comprises the compound of claim 16 and a pharmaceutically acceptable carrier or excipient.

18. A kit, which kit comprises the compound of claim 16, or a pharmaceutically acceptable salt thereof, and an instruction for using said compound or pharmaceutically acceptable salt in treating or preventing *H pylori* infection in a subject.

* * * * *

UNITED STATES PATENT AND TRADEMARK OFFICE
CERTIFICATE OF CORRECTION

PATENT NO. : 6,734,212 B2
DATED : May 11, 2004
INVENTOR(S) : Zhu et al.

It is certified that error appears in the above-identified patent and that said Letters Patent is hereby corrected as shown below:

<u>Title page,</u>
Item [56], References Cited, FOREIGN PATENT DOCUMENTS, add -- China 01142289.0 9/26/2001 --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,734,212 B2
APPLICATION NO. : 09/975136
DATED : May 11, 2004
INVENTOR(S) : Zhu et al.

It is certified that error appears in the above-identified patent and that said Letters Patent is hereby corrected as shown below:

<u>Title page,</u>
Insert: Item [30] Foreign Application Priority Data,
--September 26, 2001   (CN)............ 01142289.0--.

This certificate supersedes Certificate of Correction issued March 7, 2006.

Signed and Sealed this

Twelfth Day of December, 2006

JON W. DUDAS
*Director of the United States Patent and Trademark Office*